United States Patent [19]

Spelsberg

[11] Patent Number: 5,030,417
[45] Date of Patent: * Jul. 9, 1991

[54] METHOD AND KIT TO ASSAY FOR STEROID RECEPTOR FUNCTIONALITY IN CANCEROUS CELLS

[75] Inventor: Thomas C. Spelsberg, Rochester, Minn.

[73] Assignee: Mayo Foundation for Medical Education and Research, Rochester, Minn.

[*] Notice: The portion of the term of this patent subsequent to Nov. 17, 2005 has been disclaimed.

[21] Appl. No.: 431,695

[22] Filed: Nov. 3, 1989

Related U.S. Application Data

[63] Continuation of Ser. No. 40,934, Apr. 21, 1987, abandoned, which is a continuation-in-part of Ser. No. 13,569, Feb. 11, 1987, Pat. No. 4,806,464, which is a continuation-in-part of Ser. No. 652,295, Sep. 19, 1984, abandoned.

[51] Int. Cl.$^5$ .......................................... G01N 33/574
[52] U.S. Cl. .......................................... 422/61; 424/3; 435/29; 435/34; 435/267; 435/810; 436/175; 436/501; 436/503; 436/504; 436/808; 436/813; 436/817
[58] Field of Search ................ 424/3, 7.1, 9; 436/501, 436/817, 503, 504, 808, 813, 175; 435/29, 34, 810, 267; 422/61

[56] References Cited

U.S. PATENT DOCUMENTS

| | | | |
|---|---|---|---|
| 4,215,102 | 7/1980 | Lee | 424/3 |
| 4,232,001 | 11/1980 | Jensen et al. | 436/531 |
| 4,423,151 | 12/1983 | Baranczuk | 436/817 |
| 4,433,056 | 2/1984 | Baranczuk | 436/503 |

OTHER PUBLICATIONS

T. C. Spelsberg et al., in "Clinical Laboratory Molecular Analyses," Grune & Stratton, Inc., (1985), at pp. 189-203.

I. Jung-Testas et al., *J. Steroid Biochem.*, 20, 301, (1984).
R. R. Weichselbaum et al., *J. Cell. Physiol.*, 103, 429, (1980).
D. Huchon, *Ann. Endocrinol.*, 8, 223, (1977), (English Abstract Only).
L. Laine et al., *The Lancet*, p. 168, (7-23-77).
A. G. Fazekas and J. K. MacFarlane, *The Lancet*, p. 565, (1982).
R. E. Leake et al., *Brit. J. Cancer*, 43, 59, (1981).
S. G. Korenman, *J. Clin. Endocrinol. Metab.*, 28, 127, (1968).
K. J. Andersen et al., *Anal. Biochem.*, 83, 703, (1977).
M. L. Graham, II et al., *Mayo Clin. Proc.*, 59, 3, (1984).
P. A. Boyd et al., *Biochem.*, 18, 3685, (1979).
P. A. Boyd-Leinen et al., *Endocrinology*, 111, 30, (1982).
P. A. Boyd-Leinen et al., *J. Biological Chem.*, 259, 2411, (1984).
A. Geier et al., *J. Endocrinol.*, 80, 281, (1979).
T. Thorsen, *J. Steroid Biochem.*, 10, 661, (1979).
A. G. Fazekas et al., *J. Steroid Biochem., 13, 613, (1980).*
J. K. MacFarlane et al., *Cancer*, 45, 2998, (1980).
T. Thorsen and S. K. Stoa, *J. Steroid Biochem.*, 10, 595, (1979).
Holdaway et al., *Cancer Res.*, 52, 479, (1983).
Okret et al., *Cancer Res.*, 38, 3904, (1978).
Duvivier et al., *Clinica Chimica Acta*, 112, 21, (1981).
K. Burton, *Biochem. J.*, 62, 315, (1956).

*Primary Examiner*—Christine Nucker
*Attorney, Agent, or Firm*—Merchant, Gould, Smith, Edell, Welter & Schmidt

[57] ABSTRACT

A method and a test kit for rapidly determining the presence of functional cellular steroid receptors by assaying a tissue sample for nuclear steroid or antisteroid binding is disclosed which comprises treating the tissue with collagenase, incubating the isolated cells with a labelled steroid or a labelled antisteroid capable of complexing said receptors and measuring the bound nuclear radioactivity and the DNA of the isolated cellular nuclei.

12 Claims, 7 Drawing Sheets

FIG. 1

(RECEPTOR QUANTITATION)

FIG. 2

(RECEPTOR FUNCTION)

FIG. 3

Figure 4:
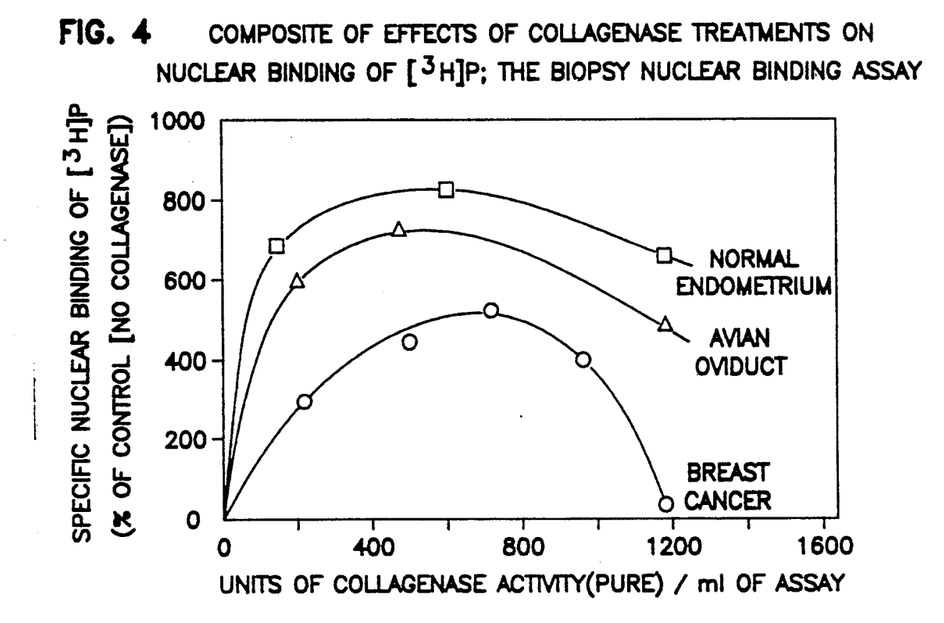

FIG. 4 COMPOSITE OF EFFECTS OF COLLAGENASE TREATMENTS ON NUCLEAR BINDING OF [³H]P; THE BIOPSY NUCLEAR BINDING ASSAY

FIG. 5

EFFECT OF [³H]E AND [³H]P CONCENTRATIONS IN MEDIA ON NUCLEAR BINDING IN THE BNB ASSAY

FIG. 6

NUCLEAR BINDING OF [³H] PROGESTERONE IN TISSUE CULTURE OF NORMAL ENDOMETRIUM AT 2°, 22°, AND 37°C

FIG. 7

STEROID SPECIFICITY OF THE NUCLEAR BINDING OF [³H] ESTRADIOL IN THE BNB ASSAY

FIG. 8

FIG. 9

Figure 10:
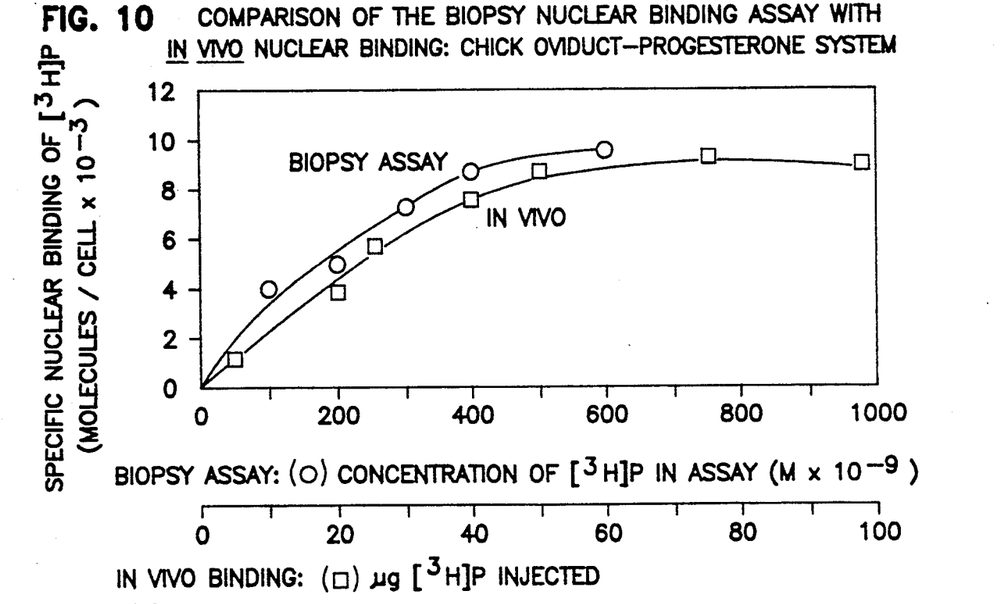

FIG. 10  COMPARISON OF THE BIOPSY NUCLEAR BINDING ASSAY WITH IN VIVO NUCLEAR BINDING: CHICK OVIDUCT-PROGESTERONE SYSTEM

Figure 11:
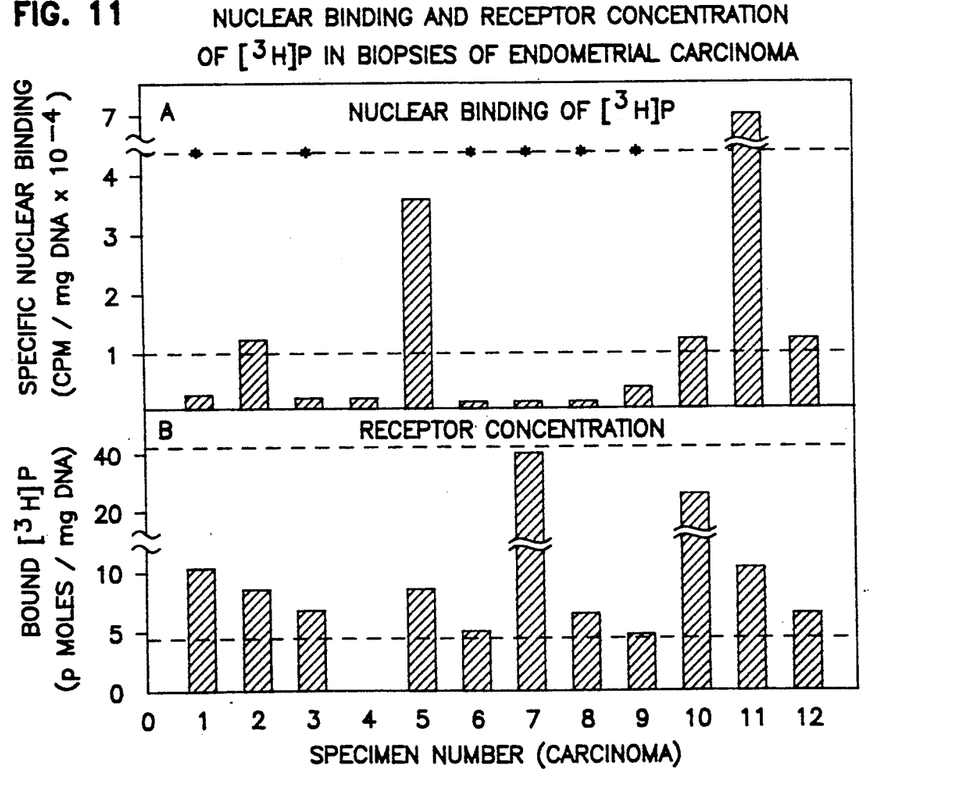

FIG. 11  NUCLEAR BINDING AND RECEPTOR CONCENTRATION OF [$^3$H]P IN BIOPSIES OF ENDOMETRIAL CARCINOMA

METHOD AND KIT TO ASSAY FOR STEROID RECEPTOR FUNCTIONALITY IN CANCEROUS CELLS

CROSS-REFERENCE TO RELATED APPLICATION

This is a continuation, of application Ser. No. 07/040,934, filed Apr. 21, 1987, now abandoned, which is a continuation-in-part of application Ser. No. 13,569, filed Feb. 11, 1987, now U.S. Pat. No. 4,806,464 which is a continuation-in-part of application Ser. No. 652,295, filed Sept. 19, 1984 now abandoned.

FIELD OF THE INVENTION

This invention pertains to a cell culture assay and to a test kit employing the assay for the determination of functional steroid receptor proteins in cells, and is specifically useful to determine the susceptibility of cancer cells from human tissue to steroid or antisteroid therapy.

BACKGROUND OF THE INVENTION

Cancer is a leading cause of death, second only to heart disease, of both men and women. In the fight against cancer, numerous techniques have been developed and are the subject of current research, directed to understanding the nature and cause of the disease, and to provide techniques for control or cure thereof.

Since most cancers occur in tissues which are steroid target tissues, treatments using steroid therapy have been useful. Some steroids (e.g., progesterone, glucocorticoids) and antisteroids (e.g., the antiestrogen, tamoxifen) inhibit cell division in most cells. The use of pharmacologic doses of estrogens, antiestrogens or reduction of estrogen (by ablative surgery) have also proven to be effective therapies for the control of breast cancer. For example, the nonsteroidal antiestrogen, tamoxifen, competes with estrogens for cytosol estrogen receptors and thus blocks the effects of estrogen in the target tissue. Progestins have been used to treat endometrial cancer and glucocorticoids have been used to treat leukemias.

Despite the above, it has been found clinically that within each class of cancer, certain populations do not respond to steroid or to antisteroid therapy. Much research has been directed to determining why this is so, both to provide a clinical diagnostic tool so that time will not be lost on steroid or antisteroid therapy for those patients having cancers that will not respond, and also to provide insight into the nature of the disease.

A known difference between steroid "target" and "nontarget" tissues is the presence of specific receptor proteins for steroids in target cells which serve as intermediaries in the action of these hormones. The generally accepted mechanism of action of steroids or antisteroid compounds in target cells is 1) entrance of the compound into cells and binding of this compound to specific receptor proteins, 2) activation of the receptor and the translocation and binding of this steroid receptor complex from somewhere in the cytoplasm or nucleus to the nuclear acceptor sites on the chromosomal material, 3) alteration of transcription of a multitude of genes into messenger RNA (mRNA), 4) processing of the mRNA, and 5) translation of these mRNAs into proteins which perform or serve a variety of functions.

Procedures have been developed to assay for the presence of these receptor proteins. In approximately 20% of cancers from steroid target tissues that have been studied, the steroid receptors are very low in concentration or are absent. As expected, these particular cancers do not respond to steroid therapy. Patients with negative receptor assays also do not respond to nonsteroidal antisteroids such as tamoxifen.

However, in studies of steroid therapy in receptor-positive cancer patients, only about half of these cancers (approximately 40% of all cancers) respond to steroid therapies. Examples of this are found in tamoxifen treatments of breast cancers and progesterone treatment of endometrial cancers. It has been speculated that the defects in the steroid action pathway are related to steps subsequent to the binding of the steroid to its receptor.

That defective (nonfunctional) receptors occur and may play a role in the nonresponse of many breast cancers to steroid therapy was reported by Leake and coworkers. As used herein with respect to receptors, the term "nonfunctional" indicates receptors incapable of activation and binding to chromosomal material. Such receptors can bind steroids or antisteroids but are otherwise defective with respect to the steroid action pathway. Studies by this group reported that 25 to 30% of 461 estrogen receptor (ER)-positive breast tumors showed no nuclear estrogen receptor (ERN), i.e., the receptors were nonfunctional (Laing et al., *Brit. J. Cancer*, 43, 59 (1977); Leake et al., *The Lancet*, 168 (1981)). In these studies, the cytosol estrogen receptor (ERC) was isolated from the tumors and the standard charcoal receptor quantitation assay performed according to the method of S. G. Korenman, *J. Clin. Endocrinol. Metal.*, 28, 127 (1968). The ERN was assayed by incubating the nuclear pellet obtained from homogenized tissue with [$^3$H]-estradiol and determining the amount of ERN present. Similar results were obtained in another laboratory using an in vitro system by incubating crude [$^3$H]-ERC with isolated nuclei and assaying the salt-extracted radioactivity (Fazekas and MacFarlane, *The Lancet*, 565 (1982)). In both studies, a 75 to 100% correlation was found between the presence of a nuclear receptor (i.e., presence of a functional receptor) and the tumor response to steroid therapy.

T. Thorsen et al., *J. Steroid Biochem.*, 10, 595 (1979) disclose a non-quantitative assay for the presence of functional nuclear steroid receptors involving the incubation of whole tissue slices with non-saturating amounts of [$^3$H] estradiol.

Thus, assays effective to measure functional/nonfunctional steroid receptors allow a more accurate prediction of which patients will or will not respond to steroid or to antisteroid treatment than do assays which simply determine the presence or absence of receptors. Reliable assays of this type will greatly assist the clinician in planning a course of treatment for these patients and would avoid the loss of treatment time due to the use of ineffective therapy. Although the Leake and MacFarlane methods have demonstrated success in discriminating between functional and nonfunctional nuclear receptors, a need exists for improved nuclear binding assays which (a) are able to analyze the functionality of all of the receptors in a cell, (b) do not require the isolation of the nuclear receptor, (c) do not require cell-free incubations, (d) require less tissue and/or (e) can be performed rapidly with readily-available equipment.

BRIEF DESCRIPTION OF THE INVENTION

The present invention is directed to a cell culture assay and a test kit for carrying out the assay which can rapidly and accurately identify whether or not tumor cells have functional steroidal receptors. The method measures the amount of nuclear-bound steroid or antisteroid in the cells. This assay gives the investigator a rapid indication as to how much biologically-active receptor is present per mg DNA or per cell. The assay requires significantly less tissue and is believed to be more rapid than those assays requiring receptor isolation and quantitation or than those involved in measuring receptor translocations in a cell-free system. The assay may be referred to herein as the "biopsy nuclear binding assay" or "BNB."

In its broadest embodiment, the present method comprises:

(a) fragmenting a tissue sample, such as a sample of carcinoma tissue, into pieces containing intact cells;
(b) digesting said fragmented tissue with collagenase;
(c) isolating the cells from said digested tissue;
(d) incubating said cells with an amount of a radiolabelled steroid or a radiolabelled antisteroid capable of complexing with and saturating the cellular steroid receptors;
(e) isolating the cellular nuclei; and
(f) measuring the bound radioactivity and the total DNA of said nuclei.

The test kit is described in detail hereinbelow.

As used herein, the term "steroid" is intended to refer to those biologically-active, natural or synthetic, polycyclic compounds which comprise a fused-reduced or partly-reduced, 17-carbon, 4-ring system cyclopentanophenanthrene. Most steroids also have two methyl groups and an aliphatic side chain attached to the nucleus. The length of the side chain varies, and generally contains 8, 9 or 10 carbon atoms in the sterols, 5 carbon atoms in the bile acids, 2 in the adrenal cortical steroids, and non in the estrogens and androgens. Known steroids which are derivatives of costisol, progesterone, testosterone and estradiol are listed in *Steroid-Cell Interactions*, R. J. B. King, et al., eds., University Park Press, Baltimore, Md. (1974), at pages 391-395, the disclosure of which is incorporated by reference herein. Steroids employed to study the specificity of cellular estrogen, progestin, androgen, mineralocorticoid and glucocorticoid receptors are listed in J. Delettre et al., *J. Steroid Biochem.*, 13, 45-59 (1980), the disclosure of which is incorporated by reference herein. Commercially-available steroids are listed in Sigma Price List, Biochemical and Organic Compounds, Sigma Chem. Co., St. Louis, Mo. (February 1986) at pages 59-64.

As used herein, the term "antisteroids" refers to compounds which do not possess the cyclopentanophenanthrene ring system of the steroids, but which are capable of significant binding to functional cellular steroid receptors. Therefore, the term "antisteroids", as used herein, is intended to encompass compounds which possess both steroidal activity as well as those which are "antihormal", i.e., which at to inhibit the activity of steroids. Many of these antisteroids, such as the anti-estrogens, are formally derivatives of stilbene, 1,2-diphenylethane, and di- and tetrahydronaphthalenes.

Known stilbene-type antisteroids include the tamoxifen, cis- and trans-clomiphene, 1-nitro-1-phenyl-2-(4-hydroxyphenyl or anisyl)-2-[4-(2-pyrrol-N-ylethoxy)-phenyl] ethylene (CN-55,945), trans-1,2-dimethyl-1,2-(4-hydroxyphenyl)ethylene (trans-dimethylstilboestrol), trans-diethylstilboestrol, and 1-nitro-1-phenyl-2-(4-hydroxyphenyl)-b 2-[4-(3-dimethylaminopropyloxy)-phenyl] ethylene (GI-680).

Known 1,2-diphenylethane-type antisteroids include cis-1,2-anisyl-1-[4-(2-diethylaminoethoxy) phenyl] ethane (MRL-37), 1-(4-chlorophenyl)1-[4-(2-diethylaminoethoxy)phenyl]-2-phenyl ethanol (WSM-4613); 1-phenyl-1[4-(2-diethylaminoethoxy) phenyl]-2-anisyl-ethanol (MER-25); 1-phenyl-1-[4-(2-diethylaminoethoxy)phenyl)-2-anisyl-ethane, mesobutoestrol (trans-1,2-dimethyl-1,2-(4-hydroxyphenyl)-ethane), meso-hexestrol, (+)hexestrol and (−)-hexestrol.

Known naphthalene-type antisteroids include nafoxidine, 1-[4-(2,3-dihydroxypropoxy)phenyl]-2-phenyl-6-hydroxy-1,2,3,4-tetrahydro-naphthalene, 1-(4-hydroxyphenyl)-2-phenyl-6-hydroxy-1,2,3,4-tetrahydronaphthalene, 1-[4-(2-pyrrol-N-ylethoxy)-phenyl]-2-phenyl-6-methoxy-3,4-dihydronaphthalene (U11,100A), and 1-[4-(2,3-dihydroxypropoxy)phenyl]-2-phenyl-6-methoxy-3,4-dihydronaphthalene (U-23,469).

Known antisteroids which do not fall anywhere within these structural classifications include coumetstrol, biochanin-A, genistein, methallenestril, phenocyctin, and 1-[4-(2-dimethylaminoethoxy)phenyl]-2-phenyl-5methoxyindene (U,11555). In the nomenclature employed hereinabove, the term "anisyl" is intended to refer to a 4-methoxyphenyl group.

The pharmaceutically-acceptable inorganic and organic acid amine salts of the amino group-containing antisteroids are also included within the scope of the term "antisteroid", as used herein, and include citrates, tartrates, acetates, hydrochlorides, hydrosulfates and the like.

The binding affinities of these compounds to steroid receptors relative to the binding of the "natural" steroid varies widely. For example, the antisteroid compounds listed hereinabove have been primarily characterized in terms of their antiestrogenic activity. While meso-hexestrol exhibits three times the binding affinity of estradiol to estrogen receptors in rate cytosol, compound U23,469 exhibits only about 40% of the binding affinity of estradiol to estrogen receptors in the same competition assay.

DETAILED DESCRIPTION OF THE INVENTION

According to the method of the present invention, the tissue to be assayed is treated with collagenase under controlled conditions. The cells are isolated intact and incubated with the appropriate radiolabelled steroid or antisteroid. The cellular nuclei are isolated, and the bound steroid or anti-steroid measured. The nuclei obtained from surgical biopsies of 10 mg (wet wt.) or more are then hydrolyzed and assayed for DNA by a standard method such as the diphenylamine assay. (Burton, *Biochem. J.*, 62, 315 (1956). The diphenylamine assay can also be conducted as a "mini-assay" which is capable of detecting 0.1-5 μg DNA per assay and allows analyses of 1 to 10 mg biopsy specimens. This method involves extraction of the nuclear pellet with ethanol, and measuring the radioactivity of the isolated extractant. The extracted nuclear pellet is then analyzed for DNA by the Burton method.

Alternatively, when using very small tissue samples, half of the nuclei are not filtered but are used for the measurement of the DNA by a fluorescence assay (ethidium bromide). The latter assay is about 50 times more sensitive than the diphenylamine method. Since DNA quantitation is the limiting factor when using very small biopsies, utilization of the fluorescence method also allows 1 to 5 mg biopsy sections to be analyzed for both functional receptors and DNA.

In the practice of the present invention, normal and diseased tissue is obtained, for example, from surgical biopsies from patients with normal endometrium, from patients with previously untreated endometrial carcinomas and from patients with breast carcinomas. Cells may also be obtained from cell cultures or from blood. In the examples, all normal endometrium and lung and most carcinomas were obtained from post-menopausal female patients. Following appropriate histologic assessment, representative biopsy samples are placed in sterile buffers at ambient temperature for immediate use in the present nuclear binding assay, preferably within 2 hours of surgery. Any excess tissue can be cryopreserved for the previously-developed, standard receptor quantitation assay.

Biopsy samples from human tissue are transferred to a suitable nutrient medium and fragmented, e.g., by mincing or chopping. The resultant tissue fragments are weighed, and transferred to a nutrient medium containing collagenase. A fixed ratio of about 0.5–15 units of collagenase, preferably about 1–5 units of collagenase per mg tissue, is preferred for reduction of all tissue types. The fragments are gently disrupted and filtered. Any retained tissue is again incubated with fresh collagenase. Following a second gentle disruption, the suspension is again filtered. Cells in the filtrate are pelleted by centrifugation and washed.

The final cell pellet is resuspended in a nutrient medium for the incubations with radiolabelled steroids or antisteroids. Radiolabelled steroids and antisteroids may be produced by a wide variety of synthetic techniques which are well known in the art. Methods for labelling steroids and antisteroids with deuterium and tritium are set forth in *Methods in Enzymology*, S. P. Colowick et al., eds., Academic Press, N.Y. (Vol. IV, 1957) at pages 732–737, the disclosure of which is incorporated by reference herein. Such techniques include the platinum-catalyzed exchange of carbon-bound hydrogen by deuterium or tritium in solutions or suspensions of the steroid or antisteroid in $D_2O$ or $T_2O$. Tritiated steroids or antisteroids can also be prepared by the hydrogenation of suitably-substituted steroids or antisteroids, e.g., those comprising halogen, CH=CH or —S— moeties. Chemical reduction reactions using tritiated metal hydrides can also be employed and ketonic compounds can be enolyzed in the presence of $T_2O$ and alkali. Tritium water has been employed for the biosynthetic preparation of steroids containing tritium in amounts adequate for further biological assays.

A wide range of additional labelling techniques are disclosed in Feteanu et al., "Labeled Antibodies in Biology and Medicine", pages 214–309 (McGraw-Hill Int. Book Co., New York (1978)). The introduction of various metal radioisotopes may be accomplished according to the procedures of D. J. Hnatowich et al., *Science*, 220, 613 (1983); Wagner et al., *J. Nucl. Med.*, 20, 428 (1979); Sundberg et al., *J Med. Chem.*, 17, 1304 (1974); and Saha et al., *J. Nucl. Med.*, 6, 542 (1976).

Among the radioisotopes used, x-ray-emitters, gamma-emitters, positron-emitters, and fluorescence-emitter are suitable for receptor quantitation, while beta-emitters and alpha-emitters can also be used for therapy.

Suitable radioisotopes for labelling steroids or antisteroids include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhnium-105, Rhenium-101, Scandium-47, Tellurium-121m, Tellurium-122m, Tellurium-125m, Thulium-165, Thulium-167, Thulium-168, Technetium-99, Copper-67, Fluorine-18, Yttrium-90, Gold-199, Palladium-100, Bismuth-217 and Antimony-211. Preferred radioisotopes for labelling compounds intended for use as therapeutic as well as receptor quantitation agents include Iodine-125, Iodine-131, Yttrium-90, Gold-199, Palladium-100, Copper-67, Bismuth-217 and Antimony-211.

One useful technique for labelling the steroidal D-ring with radioactive halogen atoms employs halogen exchange as described by R. B. Hochberg, *Science*, 205, 1138–1140 (1979) and R. B. Hochberg et al., *PNAS USA*, 77, 328–332 (1980). Acetylated steroids can be directly halogenated and reduced to yield radio-labelled compounds by the method of J. A. Katzenellenbogen et al., *J. Nuclear Med.*, 23, 411–419 (1982). Halogenation of steroidal A-rings can be accomplished by mixing them with N-chlorosuccinimide (NCS) and radioactive alkali metal halogen salts as disclosed by D. S. Wilbur et al., *J. Org. Chem.*, 47, 359–362 (1982), and references cited therein.

Other useful labelling techniques involve labelling with either Iodine-131 (I-131) or Iodine-125 (I-125) using oxidative procedures wherein a mixture of radioactive potassium or sodium iodide and the steroid or antisteroid is treated with chloramine-T (N-chloro-p-toluene sulfonamide sodium salt) e.g., as reported by Greenwood et al., in *Biochem. J.*, 89, 114 (1963) and modified by McConahey et al., in *Int. Arch. Allergy Appln. Immunol.*, 29, 185 (1969).

The media of replicate assays are made about 5–50 nM in labeled steroid or antisteroid, e.g., about 10–30 nM in [$^3$H] progesterone (or [$^3$H] estradiol). Parallel duplicate incubations are typically performed with about 10–20 nM of labelled steroid or antisteroid, e.g., [$^3$H] progesterone and an excess of the corresponding unlabelled steroid or antisteroid, e.g., progesterone (or at least about 10–20 nM [$^3$H] estradiol and excess unlabelled estradiol) to determine the extent of nonspecific binding. Incubations may be carried out at about 18°–25° C. for about 0.5–1.5 hour, preferably at about 22° C. for 1.0 hr.

After the incubations, the tubes are chilled to about 0°–10° C. and mixed with cold neutral medium (e.g., 5 mM HEPES buffer). The cells are sedimented by cold centrifugation. The cellular pellet is then subjected to a micronuclear isolation method which may readily be adapted to a routine clinical laboratory setting. The cells are homogenized in a cold, neutral buffer, preferably a sucrose or glycerol-KCl-Tris-Triton-X-100 (octoxynol-9, Rohm & Haas) medium. The homogenate is layered over a cold, neutral medium containing sucrose, glycerol, Triton X-100, Tris-HCl (tris(hydroxymethyl)amino-methane hydrochloride) and KCl. The tube are centrifuged in the cold. The pellet of partially purified nuclei is resuspended in a neutral solution. An aqueous solution comprising Tris-HCl and aqueous glycerol using a weight ratio of medium to starting tissue of about 1:0.05–0.15, preferably about 1 ml per 100 m starting tissue is useful for this purpose.

The nuclei are then analyzed for nuclear binding of the [$^3$H] steroid or labelled antisteroid by collecting them on filters which were dried and assayed for DNA by acid hydrolysis of the filters and quantitating the solubilized nucleotides by the diphenylamine assay of the Burton as set forth in *Biochem. J.*, 62, 315 (1956), the disclosure of which is incorporated by reference herein. The hydrolyzed filters are then measured for radioactivity. This method allows the measurement of the total DNA and the bound radioactivity.

For the microassay of nuclear binding, which can be carried out with an initial portion of about 1–5 mg of tissue, the DNA is quantitated by the ethidium bromide fluorescence method of U. Karsten et al., *Anal. Biochem.*, 40, 135 (1972) and K. J. Anderson et al., *Anal. Biochem.*, 83, 703 (1977). In this method, aliquots of the nuclei containing about 0.5–5 μg DNA are isolated prior to filtration and treated with a protease (Pronase) and ribonuclease. The aliquots are cooled, mixed with ethidium bromide and the fluorescence determined.

Alternatively, the nuclei are sedimented into pellets, the pellets are extracted with absolute ethanol for one hour, and the nuclei are resedimented. The alcohol extract is assayed for radioactivity and the pellet assayed for DNA by a diphenylamine "mini-assay" which can detect 0.1–5 μg of DNA per assay. The method involves the extraction of the radioactive steroid from the nuclear pellet with 1.0 ml absolute ethanol containing 0.25M sodium acetate for one hour. The solution is centrifuged at 6000×g for 10 min. and the alcohol supernatant is counted in a scintillation counter. The DNA in the residual nuclear pellet is then quantitated by resuspending the pellets in 0.1 ml of 0.5N perchloric acid and heating the suspension for 15 min. at 90° C. Preferably, the heating step is carried out in a conical test tube. The Burton diphenylamine reagent (0.2 ml) is then added and the reaction mixture is covered and incubated for 18.0 hr. in the dark. The reaction mixture is then transferred to micro titre plates and the absorption is read in a micro titre plate reader to quantitate the DNA.

The [$^3$H] steroid or labelled antisteroid specifically bound in the nuclei is expressed as CPM/mg DNA, as DPM/mg DNA, as fmol/mg DNA or as molecules/cell nucleus. The specific binding is obtained by subtracting the nonspecific binding from the total binding. The [$^3$H] steroids or antisteroids are not removed by the acid hydrolysis.

The level of nuclear bound radiolabelled steroid or antisteroid required for a therapeutic tumor response to steroid or antisteroid treatment can be estimated by: a) measuring a biological response to various concentrations of unlabelled steroid or anti-steroid under similar conditions of incubation as described above, and assessing the level of nuclear-bound steroid or antisteroid using the same concentration of radiolabelled steroid or antisteroid. (The particular biological response will dictate the length of exposure required for the unlabelled steroid or antisteroid. The incubation of cells with the radiolabelled material should remain at 60 min), b) using published reports on the normal or required concentration of steroid receptor per cell nucleus for biological responses in vivo. Typical values are approximately 1000 molecules bound per cell nucleus for minimal responses and approximately 4000 to 10,000 molecules per cell nucleus for maximal responses, or c) the minimal levels of nuclear binding required for clinical response to steroid or antisteroid therapy can be more accurately determined at the end of the clinical trails. (Each responding/nonresponding tumor can be correlated with respect to its level of nuclear-bound steroid or antisteroid.)

BNB Test Kit

The components used in carrying out the BNB assay are preferably prepared and packaged as a kit. The kit will include separately-packaged reagents, media and solvents used to carry out the assay, preferably those which are not commonly found in clinical laboratories. In its broadest aspect, a test kit for assaying a tissue sample for nuclear steroid binding or nuclear antisteroid binding will comprise, separately-packaged: (a) an amount of collagenase effective to provide about 0.5–15 units of collagenase per mg of each tissue sample to be assayed; (b) an amount of a tissue culture medium or a biological buffer having a pH of about 6.5–8.0, effective to provide a digestion medium for each tissue sample and the collagenase, and to suspend the cells derived from each tissue sample; and (c) an amount of a solution in an organic solvent of a radiolabelled steroid or antisteroid capable of complexing with and saturating the steroid receptors in the cells derived from each tissue sample.

Useful solvents for the radiolabelled steroid or antisteroid include a wide variety of volatile organic solvent including methanol, ethanol, acetonitrile, ethyl acetate, methyl acetate, diethyl ether, chloroform, carbon tetrachloride, $CH_2Cl_2$ and the like. The amount of solvent can be adjusted to the amount of steroid or antisteroid so that the performed "stock solution" has a predetermined, unit concentration, e.g., the stock solution will be 50–500 nM in steroid or antisteroid. Unit aliquots of this solution can then be withdrawn, and mixed with a measured amount of a suspension of the cells isolated from the tissue sample in the tissue culture medium or the biological buffer to readily afford an incubation medium comprising the appropriate concentration of radiolabelled steroid or antisteroid, e.g., about 5–50 nM.

To facilitate carrying out the digestion step and the incubation step of the BNB assay, the amount of the tissue culture medium or the biological buffer is preferably provided as (a) a separately packaged amount effective to provide a digestion medium for said tissue sample and said collagenase, and (b) a separately-packaged amount effective to wash the digested tissue and to suspend the cells derived from said tissue. A measured amount of the cell-containing suspension is then added to the predetermined amount of steroid or antisteroid solution to yield the incubation mixture.

Many tissue culture media and biological buffers having a pH of about 6.5–8.0 which would be useful in the present kits are commercially available in the form of sterile liquids, for example, see Sigma Chemical Co., St. Louis, Mo., 1987 price list of Biochemical and Organic Compounds at pages 1280–1282 ("Prepared Media and Balanced Salt Solutions") and 1306–1307 ("Biological Buffers"), the disclosure of which is incorporated by reference herein.

The test kit can also include a separately packaged amount of one, or preferably two, hypertonic protective buffers (pH about 6–8.5) which are employed to suspend the cells during the step wherein the incubated cells are disrupted and the intact nuclei are isolated. The protective buffer can comprise an aqueous solution of an amount of a polyol and an amount of an inorganic salt effective to maintain the integrity of the nuclei of the cells, as well as about 0.25-1% of a nonionic surfactant, which functions to free the nuclei of cellular debris. Preferably, the protective buffer is provided as (a) a separately packaged amount of buffer comprising about 10-20% weight-volume of glycerol, or a similar $C_2$-$C_6$ polyol; and (b) a separately packaged amount of protective buffer comprising about 10-20% weight-volume glycerol and about 1.2-1.6M sucrose or a similar sugar. These protective buffers can optionally contain a small, e.g., 0.05-0.3% (w/v) of bovine serum albumin (BSA), or an equivalent protein.

Polyols useful in these buffers include $C_2$-$C_6$ polyols containing about 2-5 hydroxyl groups, such as glycerol, sorbitol, ethylene glycol, erythritol and the like, as well as sugars such as sucrose, fructose, glucose and the like; sugar polymers such as ficoll, and polyoxy ($C_2$-$C_3$)alkylene glycols.

Inorganic salts include those commonly employed in tissue culture media and biological buffers, such as alkali metal and alkaline earth metal halides (NaCl, $MgCl_2$, $CaCl_2$, KCl and the like) as well as carbonates, bicarbonates, phosphates, sulfates and the like. Preferably, the buffers will be about 0.0025-0.25M in the inorganic salt or salt mixture.

Nonionic sulfactants useful in these buffers can be selected from a wide variety of these compounds, an extensive selection of which is listed in the 1987 price list of Biochemical and Organic Compounds, Sigma Chemical Co., St. Louis, Mo, at pages 313-316, the disclosure of which is incorporated by reference herein. One useful class of nonionic surfactants is the octoxynol series, e.g., $C_8H_{17}Ar(OEt)_{5-10}$—OH, particularly oxtoxynol-9.

The test kit can also include (a) a separately-packaged amount of a liquid reagent which can stop the incubation reaction, such as a 0.1% solution of BSA, in a suitable biological buffer, e.g., HEPES buffer, and/or (b) a separately packaged amount of a solution of an organic salt in an organic solvent which is effective for the nuclei extraction step, e.g., of 0.25M solution of NaOAc in 90% ethanol. Any other organic salt which is soluble in an organic solvent of similar dielectic constant, such as those listed hereinabove can be used. Such salts include alkali metal salts such as citrates, tartarates, oxalates, maleates, gluconates, pyruvates and the like.

Other optional components of the test kit include commercially available scintillation "cocktails" which are used to measure [$^3$H] and [$^{14}$C] radioactivity in a scintillation counter. [$I^{125}$] steroids or gamma-emitting radiolabelled steroids could also be used in the counting solution, using the appropriate gamma counter to measure the radioactivity.

The present kits can also include a separately packaged amount of an acid effective to cleave the nuclear DNA into its nucleotide base components, e.g., a solution of 0.5N perchloric acid in water; and separately packaged amounts of diphenylamine and a separately packaged amount of concentrated $H_2SO_4$ in glacial acetic acid (HOAc) for use in the quantitative Burton DNA assay. When combined, these reagents would yield an about 0.5-3% solution of diphenylamine in HOAc containing about 1.25-1.75% $H_2SO_4$. However, these optional materials would be readily available in the typical clinical analytical laboratory. Likewise, the present kit could include means to filter the digested tissue, a scalpel, centrifuge tubes, test tubes, microscope slides, microcentrifuge tubes and/or a Teflon TM glass homogenizer. The amounts of the separately packaged reagents and, optionally the apparatuses, can be readily adjusted by one of skill in the art to carry out any number of assays, e.g., on 1-10 tissue samples.

The present test kit can be employed in a BNB assay which, in one detailed embodiment, includes the steps listed on Table A, below.

Table A

Steps in Biopsy Nuclear Binding Assay

1. Weigh out about 400 mg of tissue. Mince with scalpel in petri dish in small volume of tissue culture medium or biological buffer (hereinafter "MCDB-202"). Filter through nylon mesh to retain fragments. Transfer minced pieces to flask with a mixture of 5 mg of collagenase (about 1125U of total activity) (prepared by adding 5.0 ml of the contents of a bottle containing MCDB-202 into a bottle containing 5 mg of the enzyme and mixing). Incubate in shaking water bath for 50 minutes at 37° C. Refilter contents of flask through nylon mesh and wash with 5.0 ml of MCDB-202 containing 4% bovine serum albumin (BSA is optional). Reincubate remaining tissue on mesh with a fresh portion of collagenase in MCDB-202 and wash with MCDB-202 as above. Centrifuge the combined filtered suspensions for 5 minutes at 500×g at 22° C. Rinse 3 times in MCDB-202 with 5-minute centrifugations between rinses. Suspend the final pellet in an appropriate volume of MCDB-202 for light microscopic examination for cell viability.

2. Transfer 0.1 ml of the cell suspension to Eppendorf microcentrifuge tube containing an appropriate amount of a [$^3$H] steroid. Prepare the microcentrifuge tube by first adding 10 $\mu$l of the tritrated steroid solution ($\geq$50 Ci/mmol at $10^{-7}$ molar concentration in a solution of absolute ethanol). Allow the alcohol to evaporate. The portion of cell suspension is added to give a final tritiated steroid concentration of 10 nM. Incubate the cells and the steroid for 1 hour at 22° C. Stop reaction by adding 1 ml cold HEPES with 0.1% BSA.

3. Chill the solution at 4° C. on ice for 5 minutes and centrifuge at 2000 rpm, 5 minutes at 4° C. Aspirate supernatant. All remaining steps are carried out with ice cold solutions.

4. Bring up pellet in 1.0 ml protective buffer A (10% w/w glycerol, 0.1% v/v Triton TM X-100, 0.01M KCl, 0.1% (w/v) BSA (optional) and 0.05 Tris-HCl, pH 7.4) at 4° C.

5. Transfer cell suspension to glass Dounce homogenizer. Homogenize 5-6 strokes with Teflon TM pestle inserted in power drill.

6. Transfer homogenate into Eppendorf tube over 0.5 ml protective buffer A plus 1.4M sucrose.

7. Centrifuge the Eppendorf tubes at 5000 rpm for 20 min. Aspirate supernatent.

8. Rinse with 1 ml of protective buffer A, centrifuge and aspirate as above. (Can freeze pellet now if needed.)

9. Ethanol extract pellet by adding 1 ml of 0.25M NaOAc in 90% ethanol and rock for 1 hour on a rocking platform.

10. Centrifuge at 2000 rpm, 5 minutes at 4° C. to sediment the nuclei.

11. Add the alcohol supernatant to 10 ml of a counting solution, e.g., Beckman HP-B counting solution, in a scintillation vial and measure the radioactivity in a scintillation spectrometer.

12. Prepare DNA standards (0–25 μg) in microfuge tubes. Add 0.1 ml 0.5N HClO$_4$ to samples and standards and heat at 90° C. for 15 minutes.

13. Add 0.2 ml of the Burton diphenylamine reagent (prepared by adding the contents of a vial containing a measured amount of HOAc and concentrated H$_2$SO$_4$ to a vial containing a measured amount of diphenylamine) to each tube and cover overnight in dark. The tubes are ready for analyses of DNA by absorbance. Use step 14 or 15 for this measurement.

14. Transfer 0.2 ml from the tubes in step 13 to a microtiter plate. Read on plate reader at 600 nm with a 490 nm reference beam or read optical density manually at 600 nm; or 15. If using a standard spectrophotometer, add 1.0 ml of the mixture of H$_2$SO$_4$ and HOAc to the tubes in step 13 instead of taking aliquots as in step 14. Read absorbance at 600 nm.

16. Calculate the μg DNA per assay using the absorbances in the standard DNAs as reference. Then calculate the dpm (bound [$^3$H] steroid) per mg DNA per assay followed by the fmol [$^3$H] steroid/mg DNA, and the molecules [$^3$H] steroid/cell nucleus.

Figure 1:
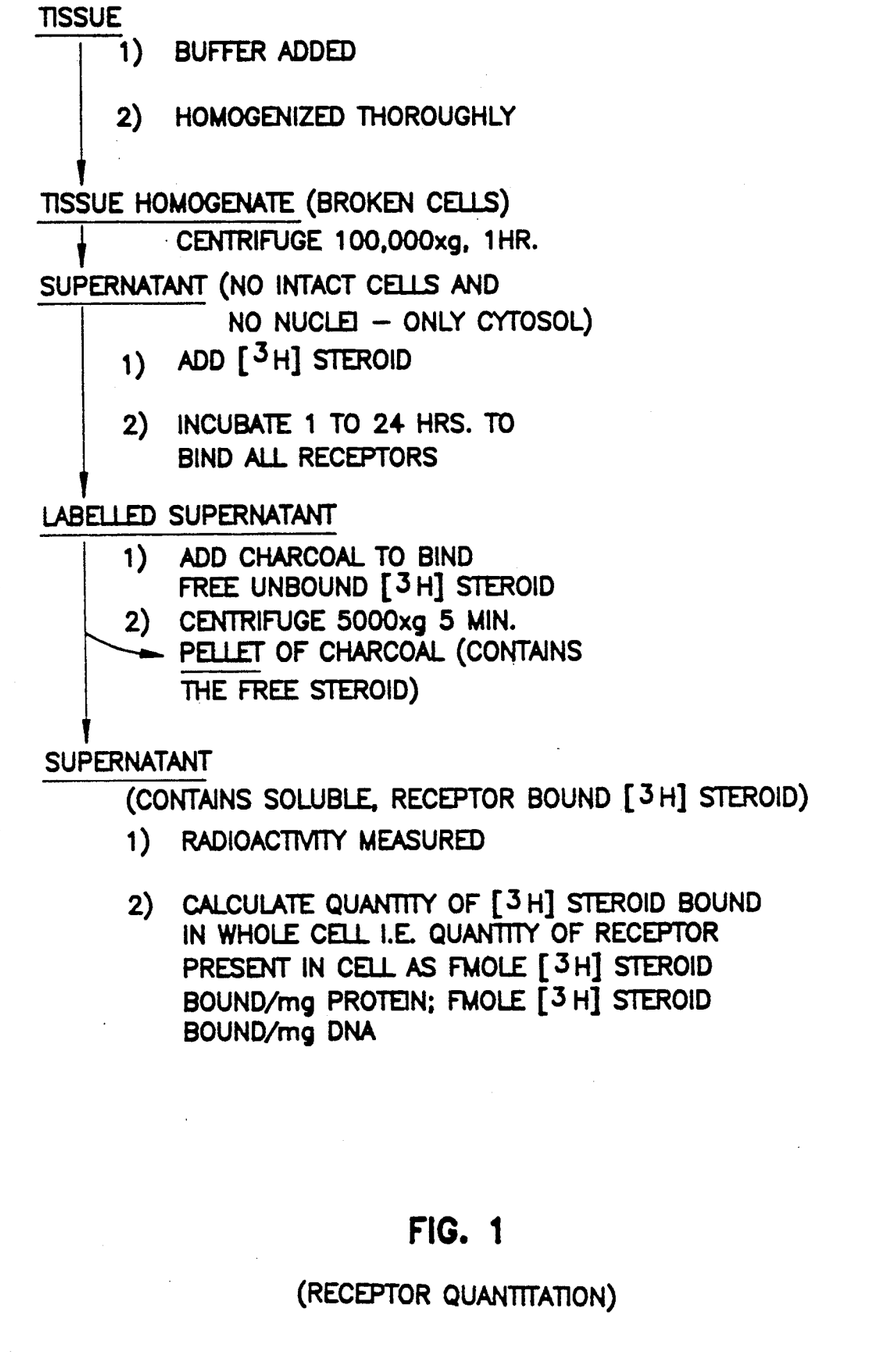
Figure 2:
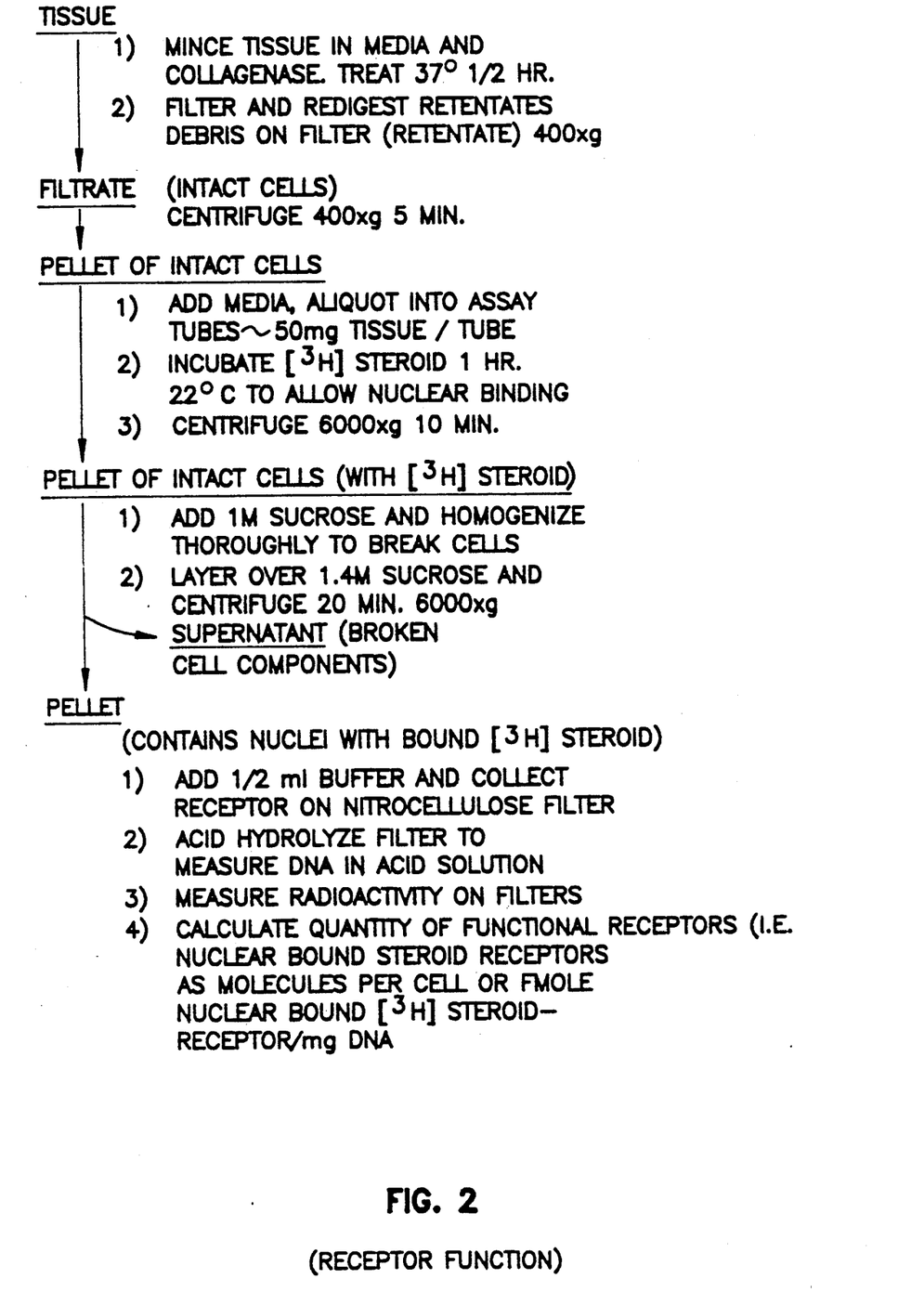

The invention will be further described by reference to the following detailed example (Example I). The conventional method is presented in detail in the Comparative Example, presented hereinbelow. The flow charts provided in FIGS. 1 and 2 are provided to facilitate a comparison between the conventional receptor quantitation method and the present BNB, respectively.

EXAMPLE I—The Biopsy Nuclear Binding Assay for Functional Steroid Receptors

The following compounds are available from the sources indicated: Tritiated and unlabelled R5020 (dimethyl-19-norpregna-4,9-diene-3,20-dione), tritiated progesterone and estrogen (40–115 C/mmole) (New England Nuclear Corp. Boston, Mass.); all other steroids and additional other chemicals are available from Sigma Co. (St. Louis, Mo.) or Fischer Scientific Co. (Pittsburgh, Pa.). All chemicals are analytical grade reagents. The steroids are routinely analyzed for degradation using high pressure liquid chromatography in a reverse phase system (uBondapak-C18 resin).

A 1.0 mg/ml collagenase enzyme preparation was used which exhibited as activity of 115–170 U per ml of preparation (CLS-III, Cooper Biomedical, Malvern, Pa.). One unit of activity will liberate from collagen 1 μmole of 1-leucine equivalents in 5 hours at pH 7.4 at 37° C. in the presence of calcium ions. Ninhydrin was used to quantitate the amino acid.

A. Collagenase Treatment of Tissue

Biopsy samples from human tissue or chick oviducts are placed in MCDB-202 medium, pH 7.4, (K. C. Biologicals, Lemexa, Kans.) at ambient temperature and transported to the laboratory. All tissue samples are then transferred to 202 medium containing 4% w/v bovine serum albumin and finely minced. The resultant tissue fragments are collected on a nylon screen by filtration, weighed, and transferred to 202 medium containing the collagenase enzyme. A fixed ratio of 2 units of collagenase per mg tissue was employed for all tissue types. A typical experiment for tissue digestion involves placing about 400 mg tissue and 2.0 units collagenase per mg of tissue in 6.4 ml 202 medium into 25 ml Ehrlenmeyer flasks and incubating at 37° C. on a rotary shaker water bath (Precision Instruments, Chicago, Ill.) at 50 rpm for 30 min. The fragments are gently disrupted by drawing them in and out of a widebore automatic pipette (25 times every 15 minutes). Following the second general disruption with the automatic pipette, an equal volume of 202 medium containing 4% BSA is added. The crude suspension is filtered through nylon gauze (500×500 micron apertures) into a small glass beaker. The fragments remaining on the filter are washed with an equal volume of the 202 medium with 4% BSA. The undigested tissue on the filter is placed in fresh enzyme solution and redigested. Cells in the filtrate are pelleted by centrifugation at 50×g for 10 min and washed twice by resuspension and centrifugation in 10 ml of 202 medium with 4% BSA. The final cell pellet is resuspended in 202 medium without BSA for incubations with labeled steroids. Cell viability is determined by the Trypan blue exclusion method, which assesses the percentage of cells in the suspensions that are not permeable to the dye. In addition, the cell ultrastructure and intact membranes are examined by microscopy. The cells obtained by the above method are then assessed for nuclear binding by steroid receptors as described below.

B. Incubation with [$^3$H] Steroids

The cells isolated from the collagenase treatment are resuspended in 0.2 ml 202 medium in a 12.0 ml test tube. This method can be used with cells from 1 to 50 mg biopsy specimens. The analyses are performed on cells isolated from fresh tissue within 2 hours of surgical removal as well as from frozen tissue. The assay can also be performed on tissue which has been stored at 4° C. in 202 medium for up to 48 hours. A minimum of four incubations are performed. The medium of two duplicates is made 25 nM in [$^3$H] progesterone ([$^3$H] P) (or [$^3$H] estradiol). Parallel duplicate incubations are performed with mixtures of 25 nM [$^3$H] P and 2.5 uM unlabelled progesterone (or 25 nM [$^3$H] estradiol and 2.5 uM unlabelled estradiol). All incubations are performed at 22° for 1 hour. For endometrial carcinomas, the progesterone receptor functionality is assessed. In breast carcinomas, both the estrogen and progesterone receptor functionalities (tissue permitting) are examined.

C. Analysis of Nuclear Binding

After the incubations, the tubes are chilled to 4° C. and mixed with 5 ml of a cold Solution A [containing 5 mM HEPES and 0.2 mM EDTA, pH 7.4 at 4° C.]. The cells are sedimented by centrifugation at 6000×g for 10 min at 4° C. The cellular pellet is homogenized in 2 ml of a cold Solution B [containing 10% (v/v) glycerol, 0.1% Triton X-100, 0.01M KCl, 0.05M Tris, pH 7.4] in a Thomas type-A glass homogenizer using a motor drive, serrated, Teflon pestle-glass homogenizer (0.001 inch clearance). The homogenate is layered over 1 ml of cold Solution C [containing 1.4M sucrose 10% (v/v) glycerol, 0.2% Triton X-100, 0.05M Tris-HCl, 0.01M KCl, pH 7.4]. The interface between the two phases are mixed and the tubes are centrifuged for 20 min at 6000×g at 4° C. The nuclear pellet is resuspended in Solution D [50 mM Tris-HCl, 10% (v/v) glycerol, pH 7.4]. Each nuclear pellet from approximately 50 mg tiss is resuspended in 0.5 ml of Solution D. The pellets of nuclei are then analyzed for nuclear binding of the [$^3$H] steroid by resuspending the pellets in 100% ethanol for 1 hour at 22° C., and then counting the alcohol in a liquid scintillation spectrometer using a PCS-xylene fluor (Amersham-Searle, Arlington Heights, Ill.). The pellets are then analyzed for DNA. This method allows the measurement of both the bound radioactivity and total DNA. Specifically, the pellets are assayed for DNA by hydrolysis of the pellets in 0.5N HClO$_4$ (90° C. for 15 min) and quantitating the solubilized nucleotides by the diphenylamine assay of Burton.

For the micronuclear binding assay, requiring less than 20 mg tissue, the DNA is quantitated by the ethidium bromide fluorescence method or by the mini-diphenylamine assay described hereinabove. In the former case, aliquots of the nuclei are taken before collecting them on the filters. The aliquots of nuclei (containing approximately 0.5 to 5 µg DNA) are treated with 0.2 mg Pronase (predigested 2 hours at 37° C.) and 0.2 mg ribonuclease (predigested 10 min. at 90° C.). The nuclear aliquots are then cooled and 2.5 µg ethidium bromide is added. The solution is mixed and the fluorescence is measured on a spectrofluorometer using an excitation of 3000 Å and an emission of 5900 Å. The specifically-bound CPM/mg DNA is calculated as the difference between the assays with [$^3$H] steroid alone and those with [$^3$H] steroid + 100-fold excess of unlabelled steroid.

Comparative Example—Isolation and Quantitation of Cellular Progesterone Receptors (PR) and Estrogen Receptors (ER)

A. Quantities of Tissues Needed for the Receptor Quantitation Assay

The quantitation of the PR and ER by the Dextran charcoal method of Korenman using a one-point determination with a nonspecific control requires a minimum of approximately 500 mg of tissue for each steroid receptor. Practically all biopsies obtained from surgery are of sufficient quantity to allow 1) the nuclear binding assay of the present invention and 2) quantitation of the receptors. Of course, the quantitation of the total receptors is not required to be performed in conjunction with the nuclear binding assay.

B. Preparation of Cytosol

All experiments are performed at 4° C. Frozen tissue is stored at −80° C. for periods not longer than two months. This storage does not cause loss in receptor quantitation. The fresh and/or frozen tissue is minced, weighed, and placed in tubes in Solution F [50 mM Tris-HCl, 1 mM EDTA, 15 mM monothioglycerol, 10 mM sodium molybdate, 2 mM PMSF, 10% (v/v) glycerol, pH 7.4]. This buffer was shown to maintain the greatest stability in the receptor preparations with the EDTA minimizing receptor aggregation, the monothioglycerol/molybdate/glycerol stabilizing the receptor and the PMSF reducing proteolysis. Briefly, frozen surgical biopsy specimens are homogenized in a Teflon pestleglass homogenizer in 4 volumes [200 µl/50 mg tissue (wet weight)] of solution F. The sample is centrifuged at 4° C. in a Beckman Microfuge for 2 min at 10,000×g to obtain the cytosol (supernatant). The pellets are saved for DNA analysis (see below).

C. Labeling and Exchange of [$^3$H] Steroid with the cytosolic Receptors

[$^3$H] R5020 (87 Ci/mmole) or [$^3$H] estradiol (102 Ci/mmole) in benzene/ethanol (9:1, v/v) are lyophilized and redissolved in an equal volume of absolute ethanol to achieve a 5 µM [$^3$H] steroid solution. Aliquots of this stock are added to the cytosol for 4 hours at 4° C. to give 100 nM [$^3$H] steroid, an amount sufficient to saturate the receptor sites. These conditions have also been shown to exchange practically all endogenous cold steroid with the [$^3$H] steroid. For the PR assay, cortisol is also lyophilized and redissolved in the same ethanol solution to give a 50 µM cortisol solution with the [$^3$H] P. This steroid eliminates the complication caused by R5020 binding to the glucocorticoid receptor. Aliquots of the crude cytosol are then used to quantitate the steroid receptor using the Dextran charcoal method described below.

D. Quantitation of the PR and ER Using the Dextran Charcoal Method

For each assay, 100 µl aliquots of each cytosol are incubated with [$^3$H] steroid in the presence and absence of the respective unlabeled steroid at 0° C. for 4 hours as described above. The synthetic progestin (R5020) is primarily used in the cytosol studied since it does not bind to serum-binding proteins which often interfere with assays. Standard progesterone may be used as a double check on the assay. For analysis of the progesterone receptor, one of the assays is made 100 nM [$^3$H] R5020 with 1 µM cortisol (to measure total binding) and half 100 nM [$^3$H] R5020 + 10 µM unlabeled R5020 + 1 µM cortisol (to measure nonspecific binding). For analysis of the estrogen receptor, one of the assays is made 100 nM [$^3$H] estradiol-17-beta + 10 µM unlabeled estradiol. Each of the incubation mixtures are then treated with three volumes (about 500 µl) of 1% (w/w) Dextran-coated charcoal suspension (10 mg charcoal and 1 mg Dextran T-70 per ml of 1.5 mM MgCl$_2$). After a five-minute incubation at 4° C., the solutions are centrifuged at 2 min at 10$^4$×g and 250 µl of each of the supernatants measured for radioactivity (i.e., receptor bound [$^3$H] steroid). The nonspecific-bound [$^3$H] steroid (assays containing labelled and unlabelled steroid) is subtracted from the total bound [$^3$H] steroid (assays containing only labelled steroid) to obtain specifically-bound [$^3$H] steroid. The latter is then plotted as fmole or pmole of bound [$^3$H] steroid per mg protein or per mg DNA for protein quantitation. For the DNA quantitation, the tissue homogenate pellets are resuspended in [0.5M NaClO$_4$] (0.1 ml/mg tissue), incubated 90° C. for 30 min and then cooled and centrifuged 1000×g for 5 min. The supernatant is then analyzed for DNA as described above, using the diphenylamine assay.

SUMMARY OF RESULTS ACHIEVED WITH THE BIOPSY NUCLEAR BINDING (CELL CULTURE) ASSAY (BNB-ASSAY)

Figure 3:
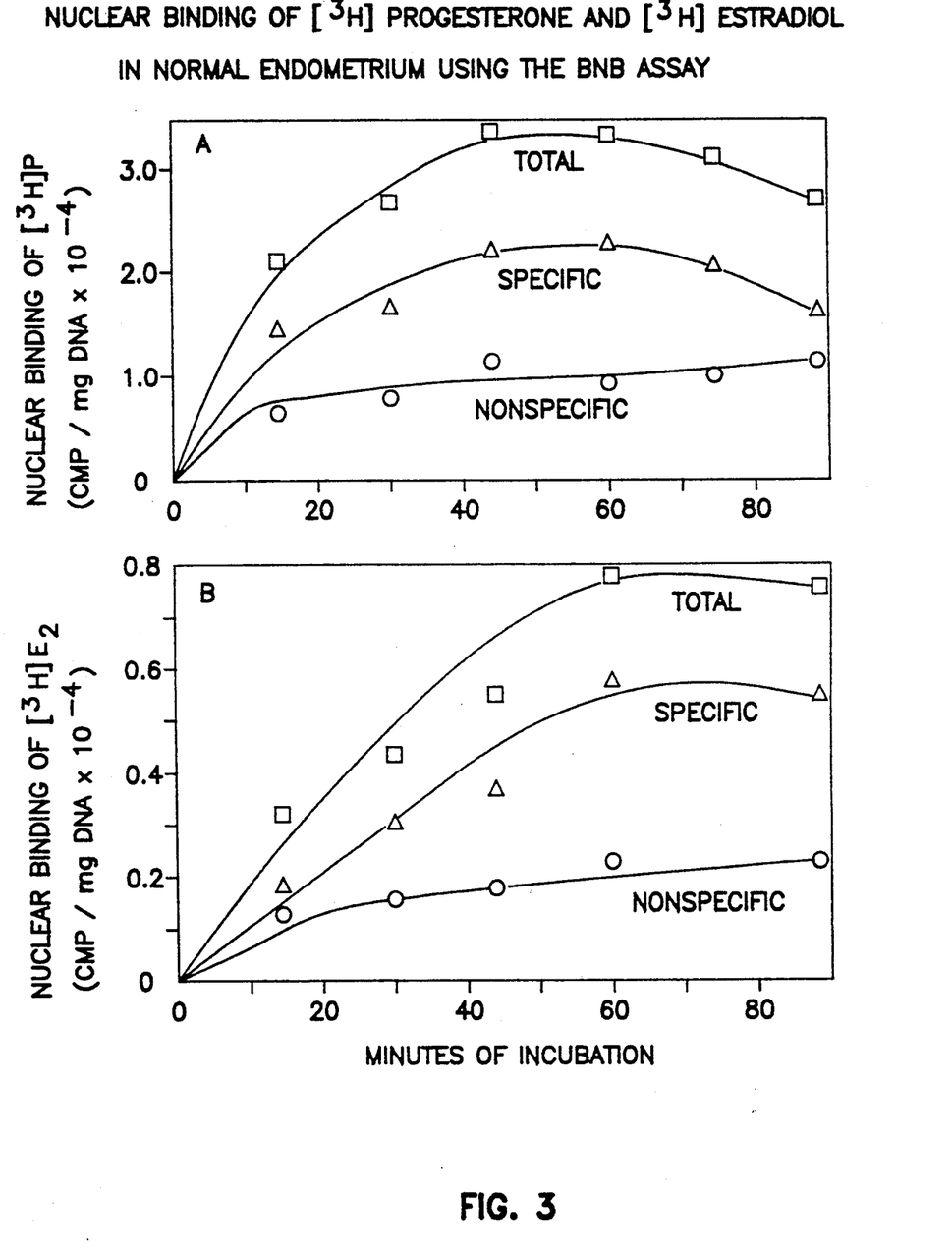

FIG. 3 shows the nuclear binding of [$^3$H] progesterone (Panel A) and [$^3$H] estrogen (Panel B) using the BNB assay. As described in the Example I, the nonspecific binding is subtracted from the total binding to obtain the specific nuclear binding of the steroids. The latter represents the specific receptor dependent nuclear binding of each of the steroids. Thus, a time-dependent specific nuclear binding can be measured and the 60-minute incubation period at 22° C. was found to be optimal.

FIG. 4 shows that the use of the collagenase to obtain isolated cells for cell culture in the assay significantly enhances the sensitivity of the assay (5-8 fold), over that of simple tissue culture. As shown, the collagenase treatment enhances the nuclear uptake of the steroids in the oviduct, breast cancer and endometrial tissues. Surprisingly, excessive collagenase treatments (higher concentrations) can inhibit the steroid receptor localization in the nuclei. About 50–1000 U of collagenase activity per ml of assay provides the best results.

Figure 5:
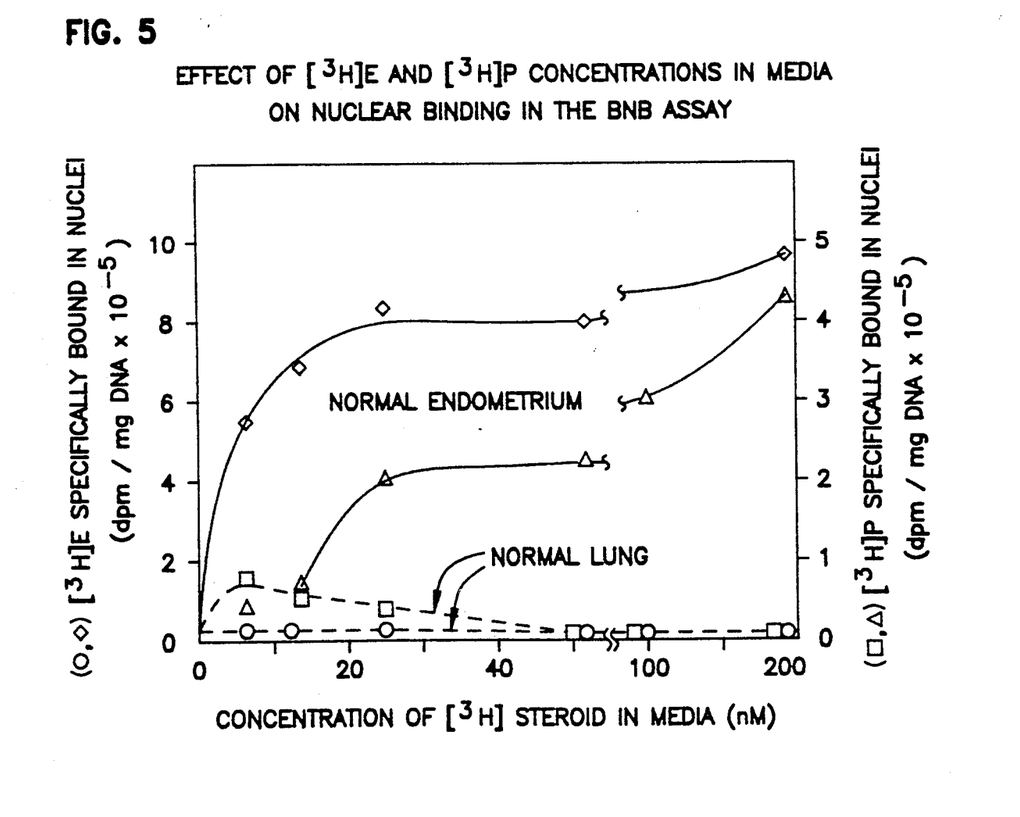

FIG. 5 shows the effects of varying the concentrations of labelled estradiol, [$^3$H] E, and progesterone, [$^3$H] P, on the nuclear binding of these steroids in normal endometrium and lung. As expected, a nontarget organ (such as normal lung) shows little nuclear binding because it does not have the steroid receptors. In contrast, since the target tissue (normal endometrium) has the receptors which are functional, a marked nuclear binding is found with a maximum binding occurring at a steroid concentration in the media of around 25 nM for each steroid. Thus, a saturable, tissue-specific nuclear binding is indicated.

Figure 6:
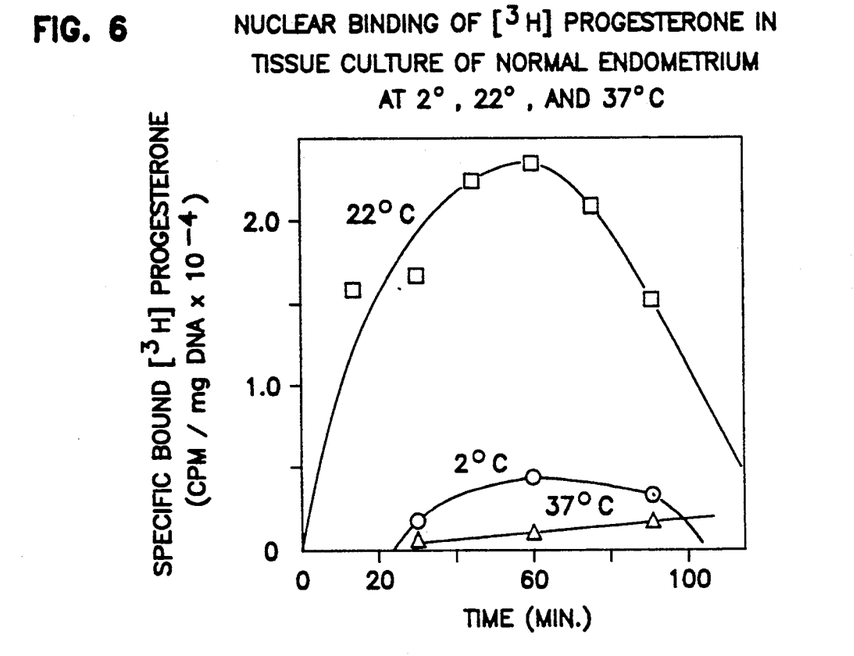
Figure 7:
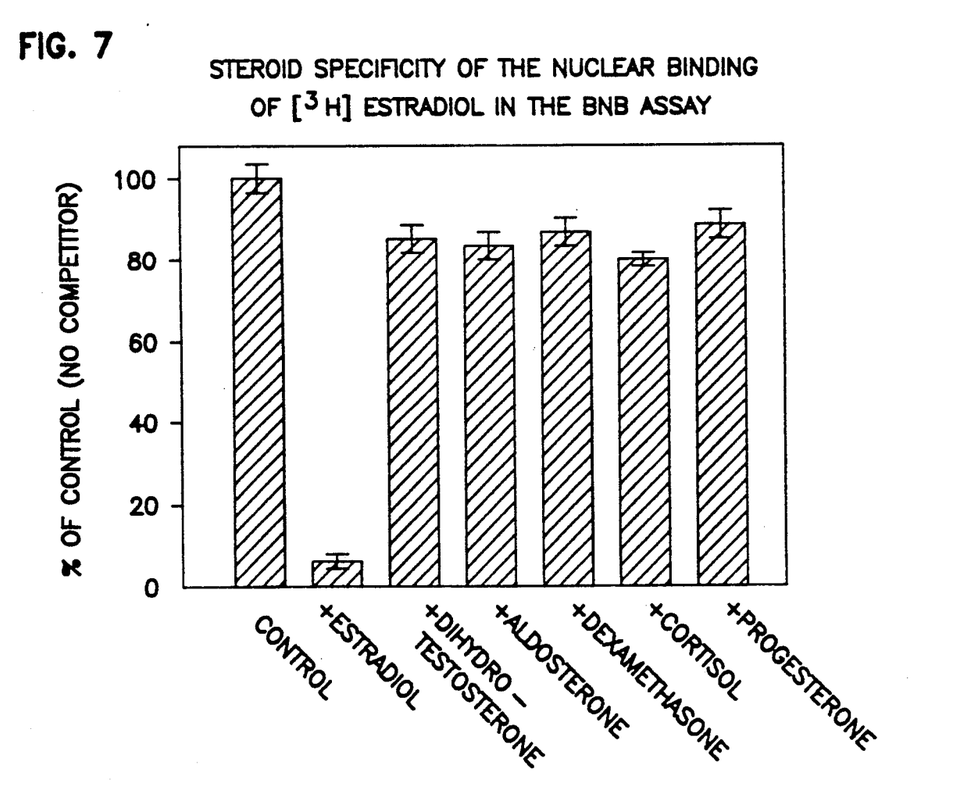

FIGS. 6–9 illustrate four basic properties of the nuclear binding of [$^3$H] P and [$^3$H] E in normal endometrium, as determined by the assay of this invention. FIG. 6 shows that at 2° C., very little specific binding occurs compared to that achieved at the 22° C. incubation. Higher temperatures show a marked inhibition of nuclear binding (e.g., 37° C.). This supports the involvement of a receptor in the nuclear binding since receptors cannot translocate and bind to nuclear sites if not allowed to "activate" as achieved by increasing the temperature over 10° C. Additional proof that a receptor is involved in the nuclear uptake of the steroid is the steroid specificity of the nuclear binding. FIG. 7 shows that only unlabelled estradiol reduces the nuclear uptake of [$^3$H] estradiol. The same effect is observed when [$^3$H] P is analyzed (data not shown). Thus, a steroid-specific, tissue-specific, time and temperature dependent, saturable nuclear binding of the [$^3$H] P has been demonstrated in the present assay. These are all properties common to receptor-dependent nuclear binding of steroids.

Figure 8:
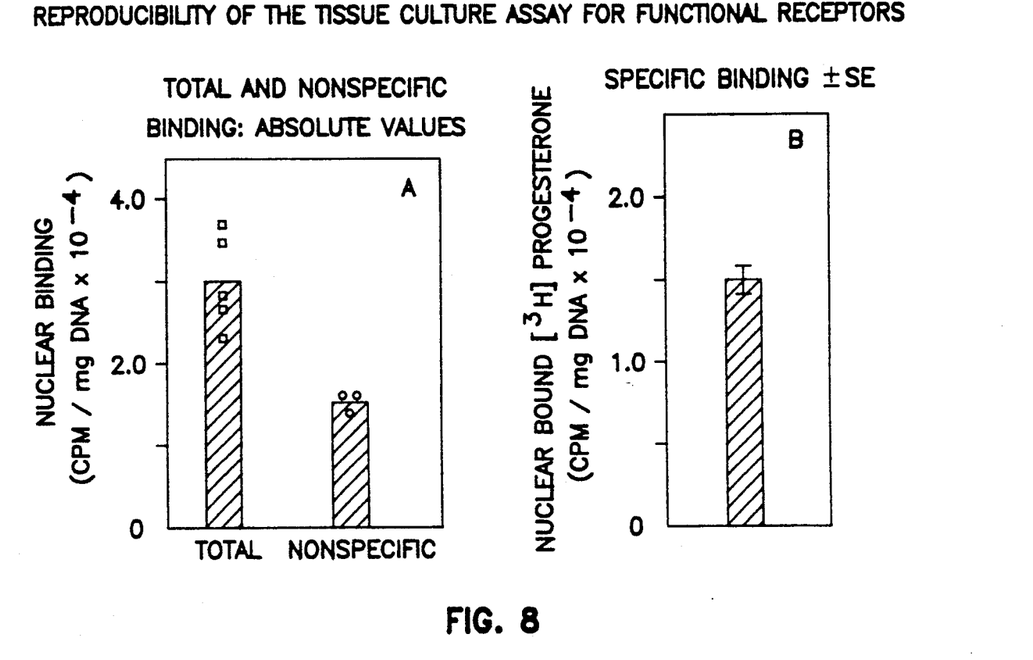

FIG. 8 shows that the nuclear binding assay is reproducible. Panel A summarizes the results of five separate assays which were performed for total binding (containing [$^3$H] steroid only). Each assay consisted of two incubations. From this value is subtracted the value obtained for the nonspecific binding (an assay containing [$^3$H] steroid + 100-fold unlabelled steroid) to give a specific binding shown in Panel B. The standard error of the calculated specific binding was ±10% S.E. of the mean.

Figure 9:
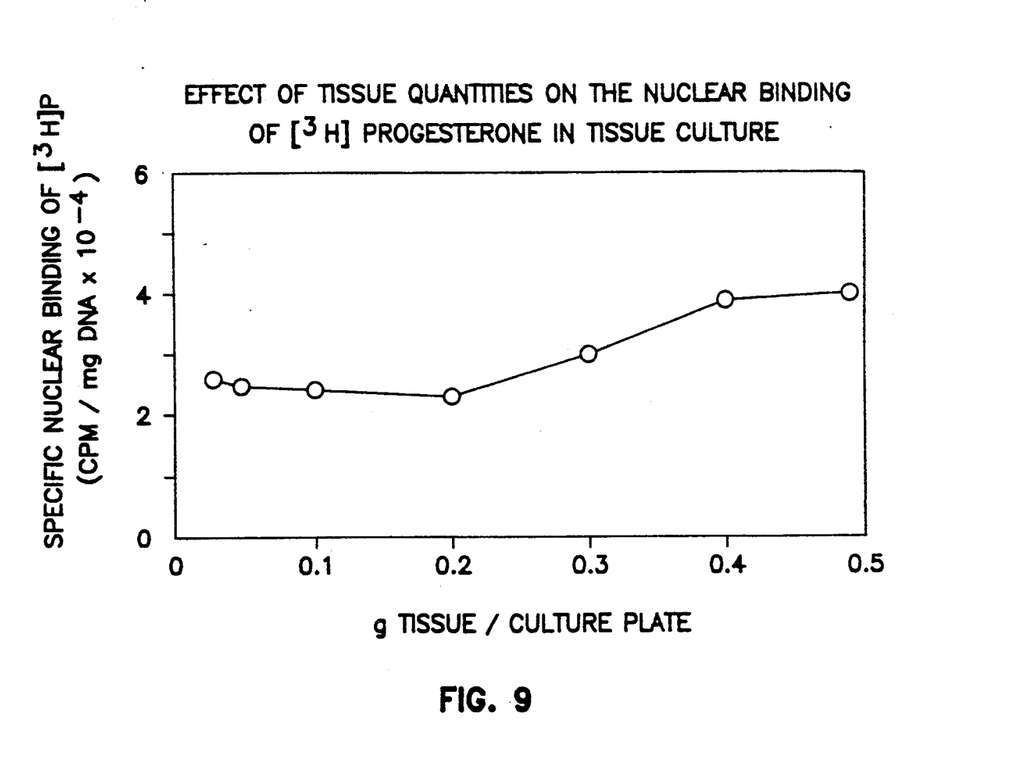

The effects of varying the quantities of the tissue on the amount of the nuclear radioactivity measured was also studied. FIG. 9 shows that 25 to 300 mg quantities of normal endometrium result in similar values for nuclear binding. Breast cancer biopsies using the present assay with the cell culture approach displayed the same properties of nuclear binding of [$^3$H] estradiol as did the studies described here using normal endometrium.

The chick oviduct was used as model system to determine whether or not the nuclear binding using the BNB assay is similar to the nuclear binding in vivo. The immature chick (7 days old) received daily injections of diethylstilbestrol (DES), 5 mg per injection, for 4 to 20 days. The oviducts in the uninjected chicks are undifferentiated but gradually undergo development during the estrogen treatment. By days 16 to 20, the oviducts are fully developed. FIG. 10 shows a comparison of the nuclear binding between in vivo conditions and the BNB assay. As can be seen, the BNB assay shows similar levels of saturation of the nuclear binding as achieved in vivo.

FIG. 11 shows the analysis of 12 patients with endometrial carcinoma. Panel A shows the results of the present BNB assay and Panel B the results of the conventional receptor quantitation assay (the Dextran charcoal absorption method). The conventional receptor quantitation assay (Panel B) indicates that 11 of the 12 patients have sufficient progesterone receptor to predict positive effects for therapy with this steroid. However, the assay of the present invention (Panel A) (the BNB assay) predicts only 5 of the 12 patients (42% of the total) will respond to this therapy. The reason for this discrepancy is that six patients (indicated by asterisks on Panel A) who have adequate PR, fail to display adequate nuclear binding of the steroid receptor. Thus, nonfunctioning receptors are indicated. More studies with the present assay have shown that of the 46 patients studied, only 17 (or 37% of the total) are predicted to respond to the progesterone therapy. Similar results have been obtained with breast cancer biopsies.

As determined by the assay of this invention, the amount of nuclear bound steroid or antisteroid gives the investigator a rapid indication as to how much "biologically active" receptor (i.e., receptor capable of binding to nuclear acceptor sites) is contained in the tumor in question (per mg DNA or per cell). It is therefore believed that this assay can as rapidly (within one day) and more accurately predict tumor response to a steroid or antisteroid compared to conventional receptor quantitation assays. Furthermore, the present assay requires about 10 times less tissue than those assays requiring receptor isolation and quantitation or than those which analyze receptor binding to isolated nuclei in a cell-free system. If desired, any excess tissue from the assay can be used to isolate the receptor for quantitative and qualitative analysis by conventional methods.

Nuclear binding defects may be primarily, if not totally, responsible for the failure of a wide variety of cancers to respond to steroid or antisteroid therapy. This would apply to such cancers as lung, breast, endrometrium, testicles, prostrate, lymphocytes and myelomas, as well as pituitary and ovary. Therefore, it is expected that the present assay will substantially enhance the clinician's ability to select the appropriate therapy to be employed which may be crucial to the effectiveness of the therapy selected.

The present assay is also expected to be useful to identify the presence or absence of functional steroid receptors in other, noncancerous pathological conditions in which steroid dependent cells are implicated. For example, the assay has positively identified functional progesterone receptors in lung tissue from a patient with pulmonary lymphangiomyomatosis. See M. L. Graham et al, *Mayo Clin. Proc.*, 59, 3 (1984), the disclosure of which is incorporated by reference herein.

The invention has been described with reference to various specific and preferred embodiments and techniques. However, it should be understood that many variations and modifications may be made while remaining within the spirit and scope of the invention.

What is claimed is:

1. A test kit for assaying one or more tissue samples for nuclear steroid binding or nuclear antisteroid binding to total nuclear bound steroid receptors comprising, separately-packaged:

(a) an amount of collagenase effective to provide about 0.5–15 units of collagenase per mg of each tissue sample;

(b) an amount of a tissue culture medium or a biological buffer having a pH of about 6.5-8.0, effective to provide a digestion medium for each tissue sample and said collagenase, and to suspend the cells derived from each tissue sample; and (c) an amount of a solution in an organic solvent of a radiolabelled steroid or a radiolabelled antisteroid capable of complexing with an saturating the steroid receptors in the cells derived from each tissue sample.

2. The test kit of claim 1 wherein the radiolabelled steroid is a tritiated steroid.

3. The test kit of claim 1 wherein the solvent is ethanol.

4. The test kit of claim 1 wherein the amount of the tissue culture medium or the biological buffer is provided as (a) a separately-packaged amount effective to provide a digestion medium for each tissue, sample and said collagenase, and (b) a separately-packaged amount effective to wash the digested tissue and to suspend the cells derived from said tissue sample.

5. The test kit of claim 1 which comprises a separately-packaged amount of radiolabelled steroid or antisteroid effective to provide an incubation medium comprising a suspension of the cells derived from each tissue sample and said tissue culture medium or said biological buffer, which incubation medium is about 5-50 nM in radiolabelled steroid or antisteroid.

6. The test kit of claim 1 wherein the radiolabelled steroid comprises [$^3$H] progesterone or [$^3$H] estradiol or any other radiolabelled steroid.

7. The test kit of claim 1 which further comprises a separately-packaged amount of a protective buffer effective to suspend the cells isolated from each tissue sample comprising an about pH 6-8.5 aqueous solution of an amount of a polyol and an amount of an inorganic salt effective to maintain the integrity of the nuclei of the cells and about 0.25-1% of a nonionic surfactant.

8. The test kit of claim 7 wherein the polyol is glycerol.

9. The test kit of claim 7 wherein the inorganic salt is KCl.

10. The test kit of claim 7 wherein the inorganic surfactant is $C_8H_{17}Ar(OEt)_{5-10}$—OH.

11. The test kit of claim 7 wherein the protective buffer is provided as (a) a separately-packaged amount of protective buffer comprising about 10-20% weight-volume glycerol and (b) a separately-packaged amount of protective buffer comprising about 10-20% weight-volume glycerol and about 1.2-1.6M of a sugar.

12. The test kit of claim 11 wherein the sugar is sucrose.

* * * * *

UNITED STATES PATENT AND TRADEMARK OFFICE
CERTIFICATE OF CORRECTION

PATENT NO. : 5,030,417

DATED : July 9, 1991

INVENTOR(S) : Spelsberg

It is certified that error appears in the above-identified patent and that said Letters Patent is hereby corrected as shown below:

Column 3, line 61, for " "antihormal" " read --"antihormonal"--.

Column 3, line 61, for "at" read --act--.

Column 4, line 4, for "-b2-" read --- 2---.

Column 4, lines 24 and 25, for "coumetstrol" read --coumestrol--.

Column 4, line 42, for "rat" read --rate--.

Column 6, line 67, for "m" read --mg--.

Column 9, lines 32 and 33, for "oxtoxynol" read --octoxynol--.

Column 12, line 62, for "tiss" read --Tris--.

Column 14, line 27, insert --with-- after the word "made".

UNITED STATES PATENT AND TRADEMARK OFFICE
CERTIFICATE OF CORRECTION

PATENT NO. : 5,030,417

DATED : July 9, 1991

INVENTOR(S) : Spelsberg

It is certified that error appears in the above-identified patent and that said Letters Patent is hereby corrected as shown below:

Column 14, line 44,45, insert "at" after the word --incubated--.

Column 17, line 8, for "an" should read --and--.

Column 18, line 4 and 5, delete "or any other radiolabelled steroid" after the --estradiol--.

Signed and Sealed this

Tenth Day of November, 1992

Attest:

DOUGLAS B. COMER

*Attesting Officer*  *Acting Commissioner of Patents and Trademarks*